(12) United States Patent
Goncharov et al.

(10) Patent No.: US 10,467,469 B2
(45) Date of Patent: Nov. 5, 2019

(54) OPTICAL SYSTEM FOR AN IMAGE ACQUISITION DEVICE

(71) Applicant: FotoNation Limited, Galway (IE)

(72) Inventors: Alexander Goncharov, Galway (IE); Christopher Dainty, Galway (IE); Istvan Andorko, Galway (IE); Peter Corcoran, Claregalway (IE)

(73) Assignee: FotoNation Limited, Galway (IE)

( * ) Notice: Subject to any disclaimer, the term of this patent is extended or adjusted under 35 U.S.C. 154(b) by 748 days.

(21) Appl. No.: 15/053,863

(22) Filed: Feb. 25, 2016

(65) Prior Publication Data

US 2016/0253559 A1    Sep. 1, 2016

Related U.S. Application Data

(60) Provisional application No. 62/126,247, filed on Feb. 27, 2015.

(51) Int. Cl.
| | |
|---|---|
| *G06K 9/00* | (2006.01) |
| *H04N 5/225* | (2006.01) |
| *H04N 5/232* | (2006.01) |
| *G02B 7/04* | (2006.01) |
| *G02B 17/08* | (2006.01) |

(Continued)

(52) U.S. Cl.
CPC .......... *G06K 9/00604* (2013.01); *G02B 7/04* (2013.01); *G02B 7/36* (2013.01); *G02B 13/007* (2013.01); *G02B 13/008* (2013.01); *G02B 13/0065* (2013.01); *G02B 13/14* (2013.01); *G02B 17/086* (2013.01); *G02B 27/286* (2013.01); *G06K 9/00241* (2013.01); *G06K 9/00255* (2013.01); *G06K 9/00288* (2013.01); *G06K 9/00617* (2013.01); *H04N 5/2253* (2013.01); *H04N 5/2254* (2013.01); *H04N 5/23212* (2013.01);
(Continued)

(58) Field of Classification Search
None
See application file for complete search history.

(56) References Cited

U.S. PATENT DOCUMENTS

| | | |
|---|---|---|
| 6,278,553 B1 | 8/2001 | Akiyama |
| 2006/0092315 A1* | 5/2006 | Payonk ................ A61B 5/0071 348/370 |

(Continued)

OTHER PUBLICATIONS

European Patent Office International Searching Authority, International Search Report and Written Opinion of Application No. PCT/EP2016/052395 filed Feb. 4, 2016, titled "An Optical System for an Image Acquisition Device", Search Report completed Jun. 30, 2016 and dated Jul. 6, 2016, 18 pages (Continued)

*Primary Examiner* — Anand S Rao
*Assistant Examiner* — Tyler B Edwards

(57) ABSTRACT

An optical system for an image acquisition device comprises an image sensor comprising an array of pixels including pixels sensitive to IR wavelengths for acquiring an image. A lens assembly includes a collecting lens surface with an optical axis, the lens assembly being arranged to focus IR light received from a given object distance on the sensor surface. The lens assembly includes at least a first reflective surface for reflecting collected light along an axis transverse to the optical axis so that a length of the optical system along the optical axis is reduced by comparison to a focal length of the lens assembly.

23 Claims, 9 Drawing Sheets

(51) Int. Cl.
*G02B 13/14* (2006.01)
*G02B 27/28* (2006.01)
*G02B 7/36* (2006.01)
*H04N 5/33* (2006.01)
*G02B 13/00* (2006.01)
*A61B 5/117* (2016.01)

(52) U.S. Cl.
CPC ............... *H04N 5/33* (2013.01); *A61B 5/117* (2013.01); *G02B 17/0856* (2013.01)

(56) References Cited

U.S. PATENT DOCUMENTS

| | | | | |
|---|---|---|---|---|
| 2007/0053075 | A1* | 3/2007 | Kamo | G02B 13/04 359/733 |
| 2008/0291531 | A1* | 11/2008 | Heimer | G02B 7/002 359/351 |
| 2010/0128937 | A1* | 5/2010 | Yoo | G06K 9/00221 382/117 |
| 2013/0336545 | A1* | 12/2013 | Pritikin | G06K 9/00892 382/116 |
| 2014/0112550 | A1* | 4/2014 | Hanna | G06K 9/00604 382/117 |

OTHER PUBLICATIONS

Dainty, et al., U.S. Appl. No. 62/035,272, filed Aug. 8, 2014 titled "Optical System for an Image Acquisition Device", 23 pages.
European Patent Office, "Communitcation pursuant to Article 94(3) EPC" dated Aug. 16, 2019 in European Application No. 16702939.6 entitled "An Optical System For An Image Acquistition Device" with a filing date of Feb. 4, 2016, 5 pages.

* cited by examiner

| Surf | Type | Radius | Thickness, mm | Glass | Diameter, mm | Conic | Comment |
|---|---|---|---|---|---|---|---|
| OBJ | STANDARD | Infinity | 400 | - | 70 | 0 | |
| 1 | COORDBRK | 0 | - | - | - | - | |
| 2 | Aperture Stop EVEN ASPH | 4.08 | 2 | 1.63 | 3.2 | -1 | S1 aspheric with 3 coeff* |
| 3 | COORDBRK | 0 | - | - | - | - | |
| 4 | STANDARD | Infinity | 0 | MIRROR | 4.1 | 0 | S2 plane mirror |
| 5 | COORDBRK | -3.9 | - | - | - | - | |
| 6 | COORDBRK | 0 | - | - | - | - | |
| 7 | STANDARD | Infinity | 0 | MIRROR | 4 | 0 | S3 plane mirror |
| 8 | COORDBRK | - | 1.5 | - | - | - | |
| 9 | EVEN ASPH | Infinity | 2 | - | 2.4 | -1 | S4 aspheric with 3 coeff* |
| 10 | STANDARD | Infinity | | | 1.09 | 0 | S5 Image plane (sensor) |

*S1  Coeff on y^4 : A= 0.0012887    Surface S1 sag is given as $z = (1/2R) \cdot y^2 + A \cdot y^4 + B \cdot y^6 + C \cdot y^8$  (R=4.08 mm)
    Coeff on y^6 : B= -0.00010986
    Coeff on y^8 : C= 2.752344e-005

*S4 Coeff on y^4 : A= 0.00755407   Surface S4 sag is given as $z = A \cdot y^4 + B \cdot y^6 + C \cdot y^8$ (1/2R=0, since it is a planoid surface)
    Coeff on y^6 : B= 0.00776547
    Coeff on y^8 : C= -0.00519217

Figure 7

OPTICAL SYSTEM FOR AN IMAGE ACQUISITION DEVICE

CROSS REFERENCE TO RELATED APPLICATION

This U.S. non-provisional patent application claims the benefit of priority under 35 USC § 119 to U.S. Provisional Patent Application No. 62/126,247 filed Feb. 27, 2015, the contents of which are expressly incorporated by reference herein in their entirety.

FIELD

The present invention relates to an optical system for an image acquisition device.

BACKGROUND

U.S. Patent Application No. 62/035,272 filed 8 Aug. 2014 (Ref: FN-397P-US) discloses an optical system for simultaneously acquiring visible and infrared (IR) images of a scene including a face having an iris pattern, with a view to acquiring a near-infrared (NIR) image of the scene where the iris pattern extends sufficiently across an image sensor to enable iris based biometric identification to be performed.

In U.S. 62/035,272, the face was typically at a distance of between 200-250 mm and the focal length required to image such a face on an 8 megapixel (Mp) sensor was approximately 4.65 mm (with a demagnification of 200/4.65=43, one could use a sensor as small as 65 mm/43=1.5 mm diagonal–65 mm being an approximate distance between eyes). Such an optical system could be incorporated within the relatively shallow housings of modern image acquisition devices including smartphones, tablets and laptop computers so enabling iris-based identification of users to such devices.

However, where users do not wish to position their face as close as 200-250 mm to an image acquisition device for identification purposes and are only prepared to be imaged at for example, 400 mm, the required focal length for an imaging system such as disclosed in U.S. 62/035,272 would increase to the point where it could not be incorporated within a shallow housing.

For example, even with a dedicated IR optical system specifically designed to image eye regions within a face, a co-axial image sensor and lens including an entrance pupil optimized to image an object such as an eye region, 40 mm in size, at a distance of 400 mm at F/2.4 would require a focal length of between f=13.7 mm and f=7.1 mm depending on the type of optics employed. (For these two examples, the demagnification would be 400/13.7=29 and 400/7.1=56, leading to the image sizes of the eye region 40 mm/29=1.4 mm and 40 mm/56=0.7 mm respectively (40 mm being the approximate size of an eye).

In order to focus on objects at variable distances, either the lens or the image sensor would need to move relative to one another. In this case the total track length (TTL) of the imaging system could have to increase to greater than between 7.1 mm and 13.7 mm, so making implementation more unfeasible within shallow housing devices.

SUMMARY

According to a first aspect there is provided an optical system for an image acquisition device. According to a second aspect there is provided a biometric recognition system.

BRIEF DESCRIPTION OF DRAWINGS

Embodiments of the invention will now be described, by way of example, with reference to the accompanying drawings, in which:

FIG. 7 illustrates aspheric coefficients for the optical systems of FIGS. 5 and 6;

DESCRIPTION OF PREFERRED EMBODIMENTS

Figure 1:
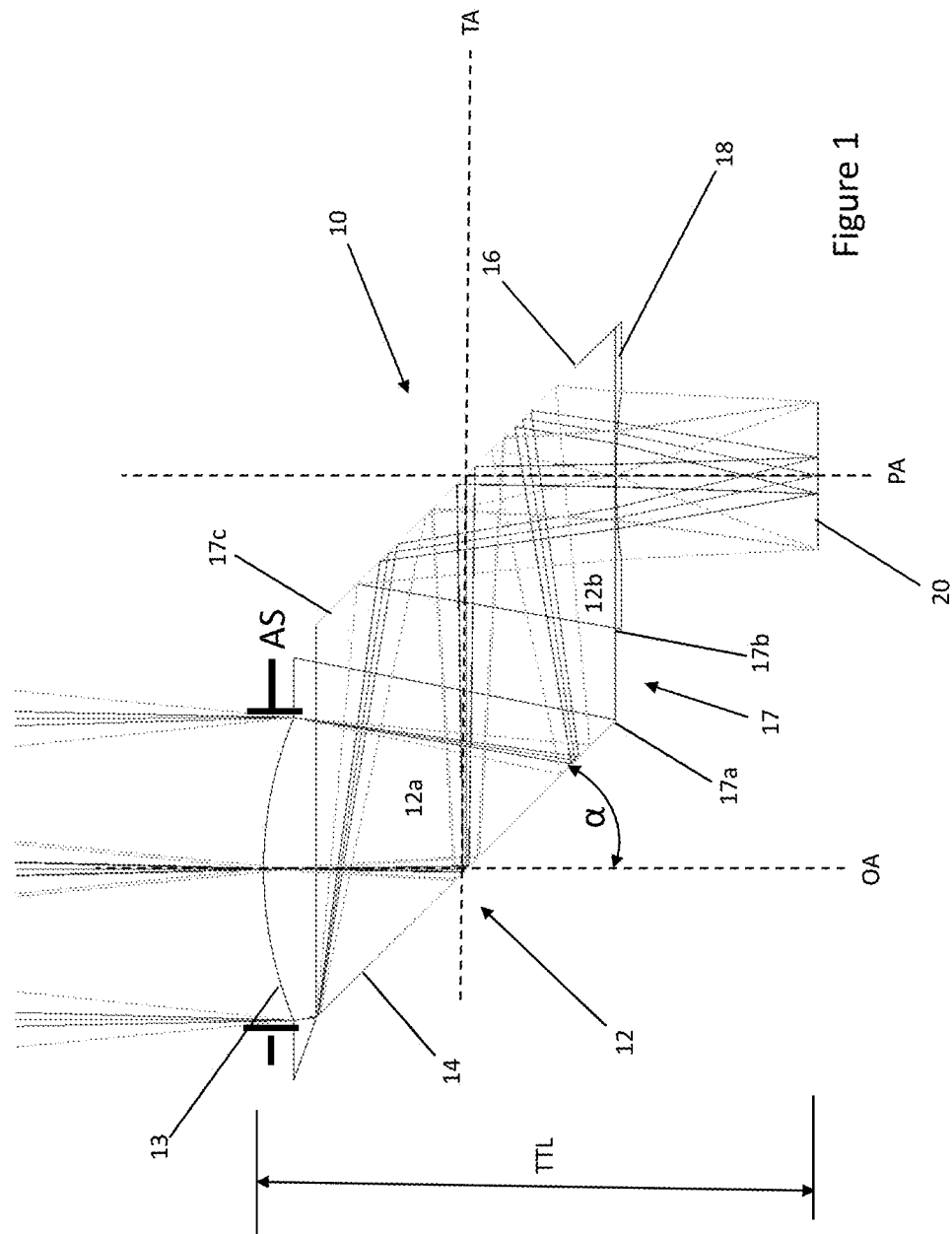
FIG. 1 is a cross section of an optical system for an image acquisition device according to a first embodiment.

Referring now to FIG. 1 there is shown in cross-section, an optical system 10 for an image acquisition device according to a first embodiment of the present invention. The optical system 10 comprises a folded lens 12 having a positive (convex) object side surface 13 with an aperture stop (AS) of approximately 3.0 mm. The object side surface 13 of the lens 12 is symmetric about an optical axis designated OA.

A first reflective surface 14 is disposed behind the object side surface 13 at an angle $\alpha$ to the optical axis OA. The surface 14 is formed of a material that reflects infrared wavelengths in the spectrum from about 750 to at least about 900 nm.

The first reflective surface 14 extends across the optical axis sufficiently to reflect all IR light collected through the object side surface 13 laterally across the optical axis OA towards a second reflective surface 16 laterally spaced apart from the first reflective surface. Again, the surface 16 is formed of a material that reflects infrared wavelengths in the spectrum from about 750 to at least about 900 nm.

In the embodiment, each of the surfaces 14 and 16 are mutually parallel, disposed at an angle $\alpha=45°$ to the optical axis and each of the surfaces 14 and 16 is disposed symmetrically about an axis (TA) running transverse to the optical axis (OA). The second reflective surface 16 thus reflects IR light reflected from said first reflective surface 14 back along an axis (PA), which extends parallel to the original optical axis OA.

Light reflected from the second reflective surface 16 is focused through a concave image side surface 18 of the lens 12, symmetric about the parallel axis PA, onto an image sensor 20, which is disposed orthogonally to and symmetric about the parallel axis PA. As will be appreciated, the image sensor 20 needs to be of the type comprising pixels, which are sensitive to at least light at IR wavelengths.

In the embodiment, the lens 12 is formed as a single piece of molded plastics material with the reflective surfaces 14 and 16 being defined by providing a coating on the two opposite lateral surfaces of the molded lens and with the object side and image side surfaces 13, 18 defined on the other two surfaces. Examples of suitable reflective coating materials for the surfaces 14, 16 include: aluminium (Al), silver (Ag), and gold (Au) and these can be provided by any suitable process including mechanical transfer or chemical deposition.

In some embodiments, the lens 12 could therefore comprise a solid parallelogram prism core with the surfaces 13, 14, 16 and 18 being defined on the peripheral surfaces of the prism. However, in order to reduce the bulk of the lens material and also improve transmissivity for light passing through the lens 12, a channel 17 is defined within the lens 12. The channel 17 has a pair of parallel spaced apart side walls 17a, 17b and extend diagonally from front to rear of the lens 12 to divide the lens into a pair of spaced apart triangular prisms 12a, 12b—a first of the prisms 12a disposed behind the surface 13 and with its lateral surface providing the first reflective surface 14 and its medial surface providing the side wall 17a. A second of the prisms 12b is disposed in front of the surface 18 and with its lateral surface providing the second reflective surface 16 and its medial surface providing the side wall 17b.

In order to allow the lens 12 to be fabricated as a single piece, in FIG. 1, the channel 17 does not extend through the full depth of the prism and a bridge section 17c connects the first and second prisms 12a and 12b. If the prisms 12a, 12b were formed separately, lens focusing could be achieved by moving the prism 12b along the TA axis. However one might get unwanted reflections from the surfaces 17a and 17b. This air spaced configuration of prisms 12a and 12b could induce aberrations on the surfaces 17a and 17b. This could be mitigated if the surfaces 17a and 17b were cut perpendicular to the TA axis to preserve the rotational symmetry of the light beam. However, the air spacing would then be reduced compared to the case with a slanted cut as shown in FIG. 1.

The lens 12 could also be provided as a number of discrete components including: a front collecting lens providing the object side surface 13, a first reflective member providing the surface 14, a second reflective member providing the surface 16 and a rear focusing lens providing the image side surface 18. However, it will be appreciated that this would increase the component count somewhat as well as requiring more complicated assembly of the system 10 to align the constituent components of the lens 12.

In any case, in the arrangement of FIG. 1, for an optical system with F/2.4 and a focal length of 7.1 mm imaging a 40 mm object at 400 mm, a total track length (TTL) of 5.5 mm can be achieved by folding the optical path of light captured by the lens 12.

It is nonetheless appreciated that in order to focus on a subject at a distance nearer than 400 mm, one of the sensor 20 or lens 12 would need to move relative to one another, so extending the TTL. Where the prism 12b moves relative to the prism 12a and the sensor, TTL is not increased, but as explained above, other drawbacks are incurred. In this regard, it will be appreciated that mechanically mounting the image sensor 20 for movement would be challenging and alternative embodiments to mitigate the need to move the lens 12 and sensor 20 relative to one another are described below.

Figure 2:
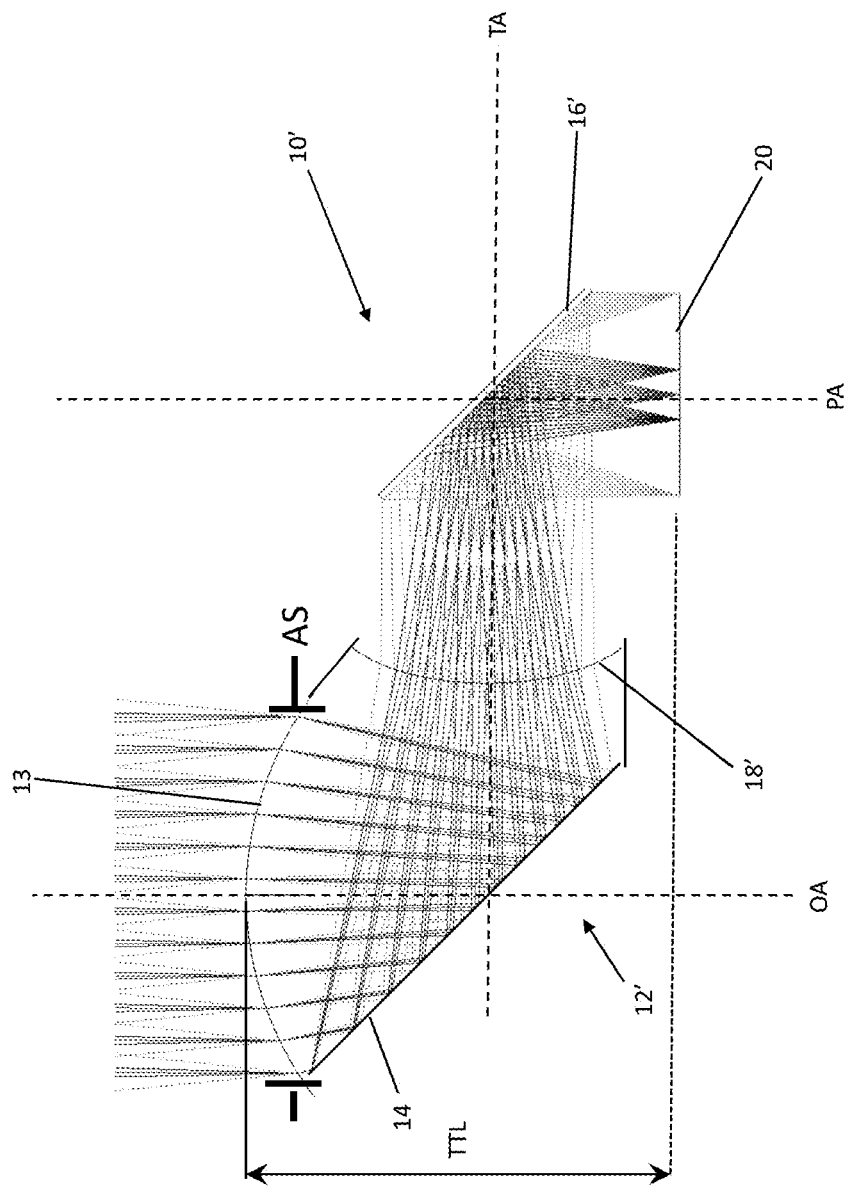
FIG. 2 is a cross section of an optical system for an image acquisition device according to a second embodiment.

Turning first to FIG. 2, an alternative embodiment of the optical system 10' includes a molded lens 12' including a shorter transmission path than either a solid parallelogram prism of the type shown in FIG. 1 or the two-part lens 12a, 12b of FIG. 1.

In this case, an object side surface 13 has an aperture stop (AS) of approximately 3.7 mm symmetric about an optical axis OA and a first reflective surface 14 are provided on the lens 12' as before. However, in FIG. 2, an image side surface 18' is defined about an axis TA transverse to the optical axis OA to focus light reflected from said first reflective surface 14.

In this embodiment, a discrete reflective member 16' disposed parallel to the first reflective surface and laterally spaced apart from the surface 18' to reflect light back along an axis (PA) extending parallel to the original optical axis OA.

Light reflected from the second reflective member 16' is focused on an image sensor 20 which is disposed orthogonally to and symmetric about the axis (PA) extending parallel to the original optical axis OA.

It will be appreciated that because of its different position along the optical path of light through the lens 12', the aspheric coefficients for the surface 18' will differ from those of the surface 18 of FIG. 1.

Nonetheless, in the arrangement of FIG. 2, for an optical system with F/2.8 and a focal length of 10 mm imaging a 40 mm object at 400 mm, a total track length (TTL) of 4.5 mm can be achieved by folding the optical path of light captured by the lens 12'.

Again, it will be appreciated that in order to focus on a subject at a distance nearer than 400 mm, one of the sensor 20 or lens 12' would need to move relative to one another, so extending the TTL. Again, alternative embodiments to mitigate the need to move the lens 12' and sensor 20 relative to one another are described below.

Figure 3:
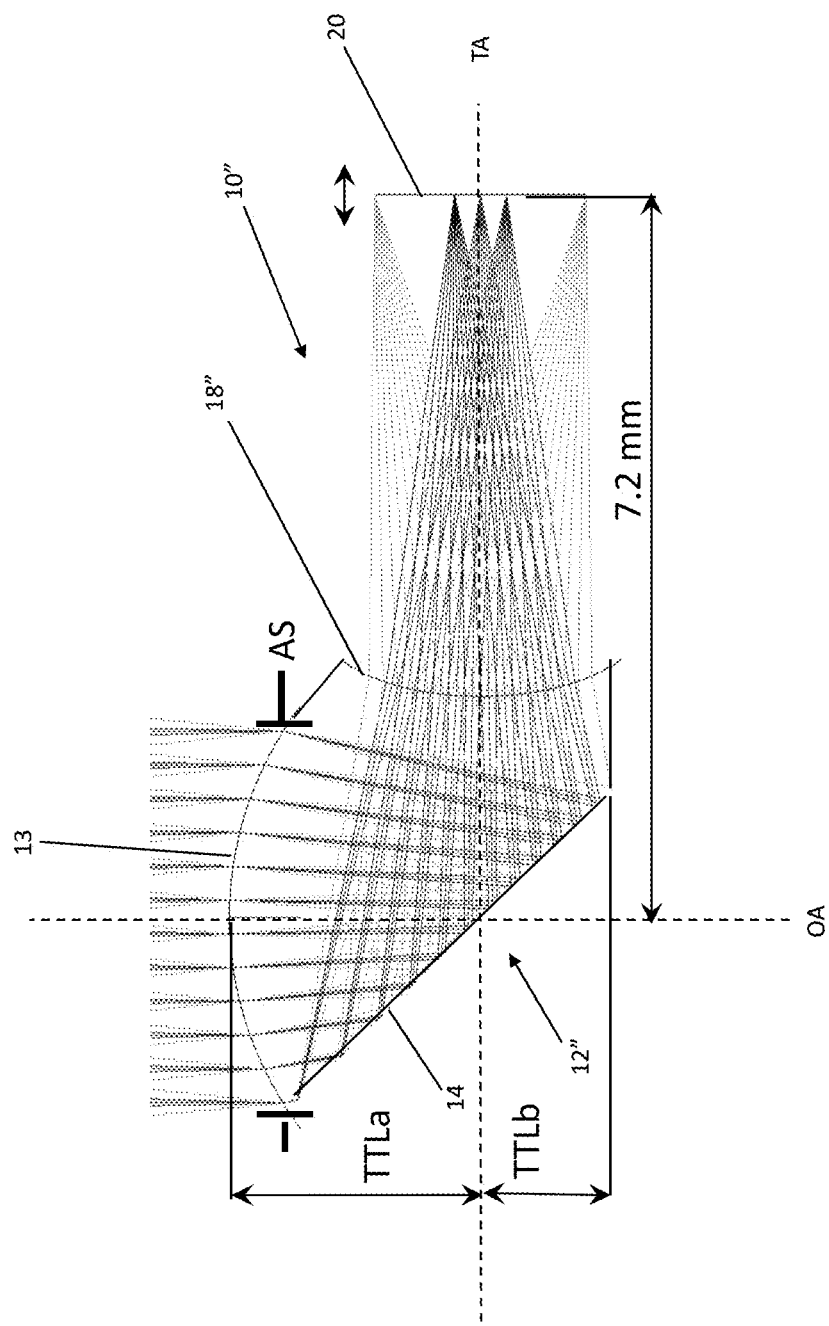
FIG. 3 is a cross section of an optical system for an image acquisition device according to a third embodiment.

Turning now to FIG. 3, there is shown a still further embodiment of the optical system 10". In this case, the lens 12" is similar in configuration to the lens 12' of FIG. 2, although the aspheric coefficients of the surfaces 13 and 18"' may differ. The aperture stop (AS) is again 3.7 mm. The principle difference however is that the reflective member 16' of FIG. 2 has been removed and the image sensor 20 is now disposed orthogonally to and symmetric about an axis (TA) running transverse to the original optical axis OA.

In the arrangement of FIG. 3, for an optical system with F/2.8 and a focal length of 10 mm imaging a 40 mm object at 400 mm, a total track length (TTL) comprising TTLa+TTLb of approximately 4.0 mm can be achieved, where TTLa=2.5 mm extends forwards of the transverse axis (TA) and TTLb=1.5 mm backwards from the transverse axis.

In this example, an object shift of 2 mm along the optical axis corresponds to 1.25 µm defocus. In this case, one of the lens 12" or the image sensor 20 could be mounted for movement along the transverse axis to maintain objects in focus. Nonetheless, it is appreciated that in spite of the minimal TTL of this embodiment, mounting a sensor 20 for movement can be challenging.

Figure 4:
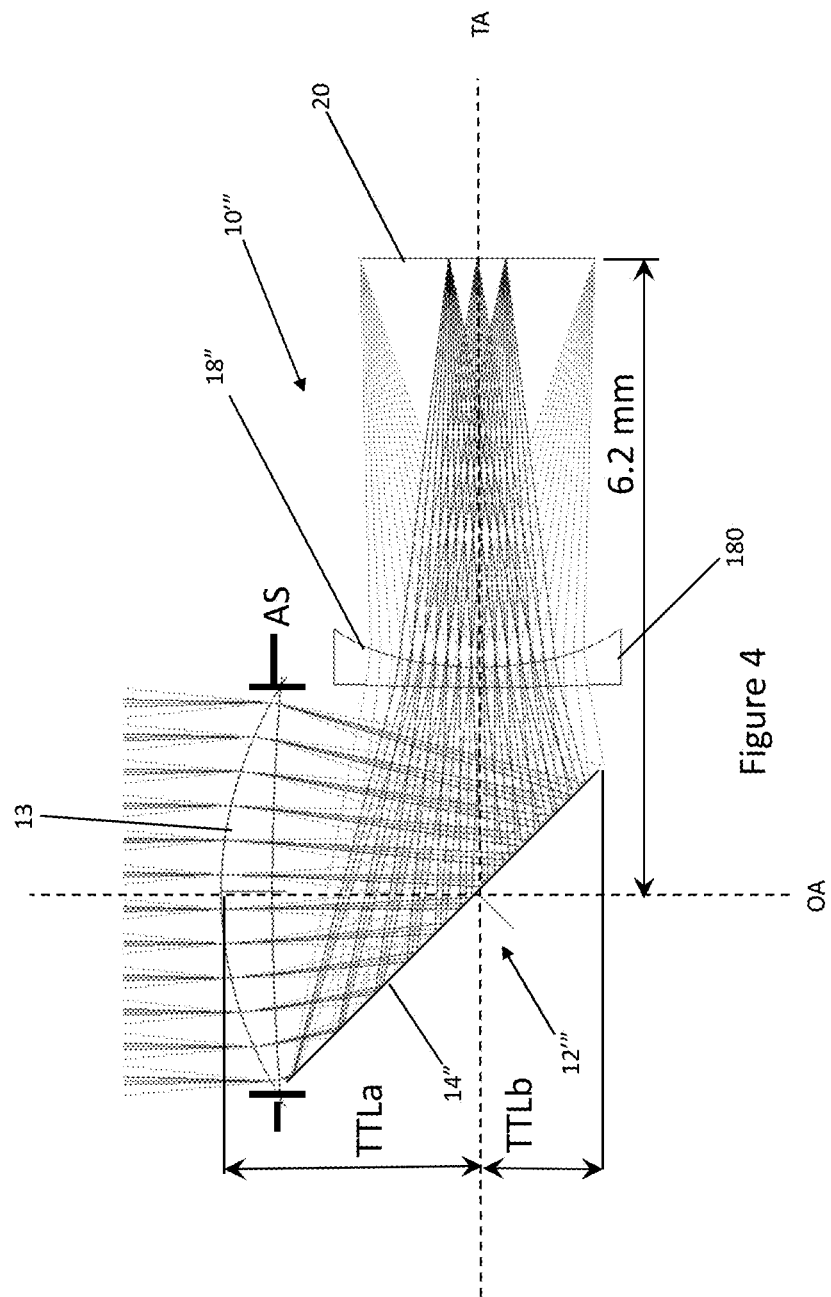
FIG. 4 is a cross section of an optical system for an image acquisition device according to a fourth embodiment.

Turning now to FIG. 4 which shows a further embodiment of the optical system 10''' involving minimal lens bulk and so transmission losses within the optical path. Optically, the lens 12''' is similar to the lens 12" of FIG. 2, except that rather than employing a monolithic piece of plastic to provide focusing, the lens 12''' comprises a number of discrete components including: a front collecting lens providing the object side surface 13, a reflective member providing the surface 14" and a transverse focusing lens 180 providing the image side surface 18"'.

In the arrangement of FIG. 3, for an optical system with F/3.0 and a focal length of 10.66 mm imaging a 40 mm object at 400 mm, a total track length (TTL) comprising TTLa+TTLb of 4.0 mm can be achieved, where TTLa=2.5 mm extends forwards of the transverse axis (TA) and TTLb=1.5 mm backwards from the transverse axis.

Again, this arrangement would increase the component count somewhat as well as requiring more complicated assembly of the system 10 to align the constituent components of the lens 12". However, instead of moving the sensor 20, the focusing lens 18" could be mounted for movement back and forth along the transverse axis TA to accommodate movement of the object.

In this example, an object shift of 2 mm along the optical axis corresponds to 1.42 μm defocus which is readily handled by moving the lens 18".

As indicated above, moving either the lens 12 or the image sensor 20 of the above-described embodiments could add complexity to implementing the invention.

Figure 5:
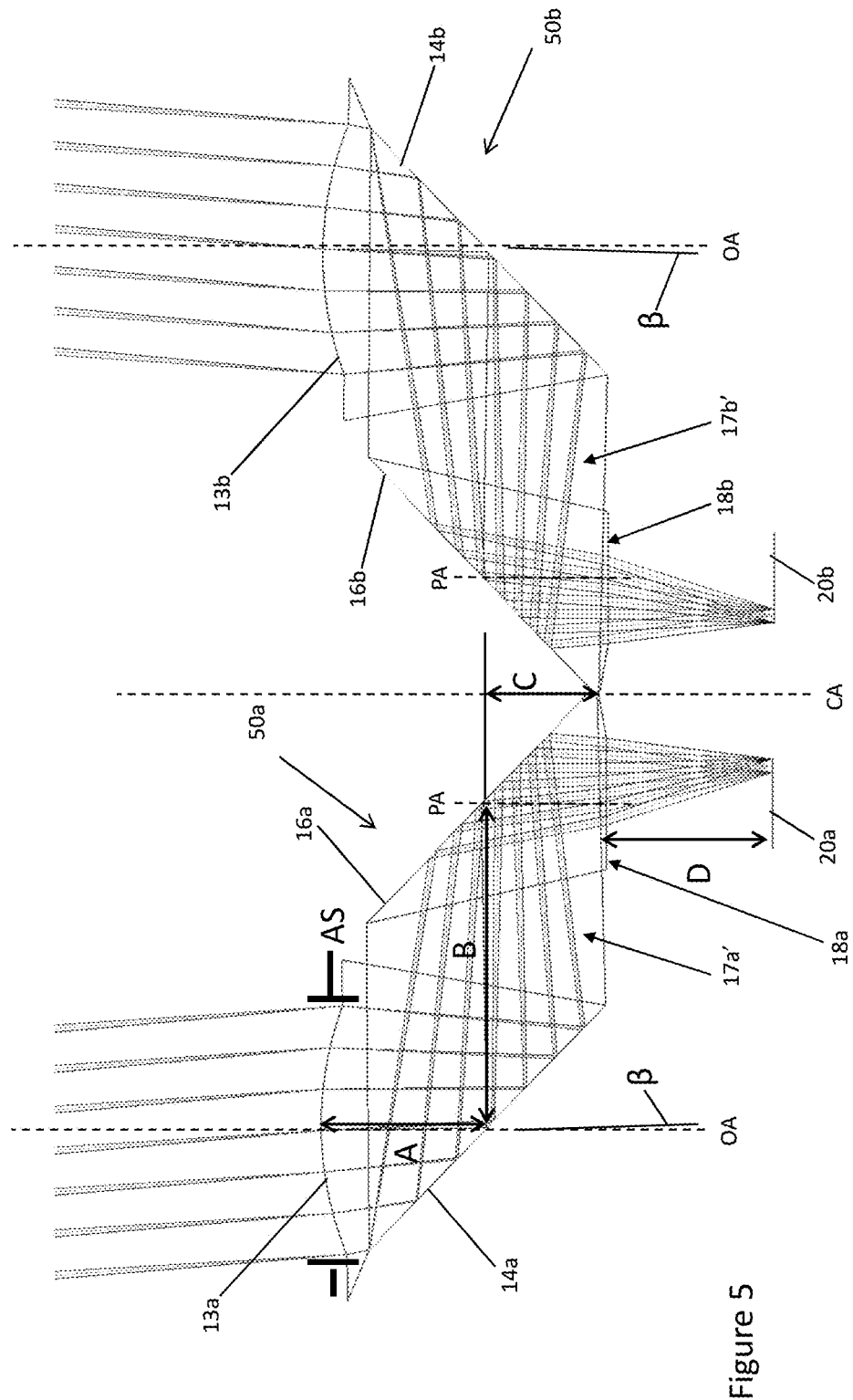
FIG. 5 is a cross section of a binocular variant of the optical system of FIG. 1 where each lens portion is arranged to accommodate movement of a subject relative to the acquisition system.
Figure 6:
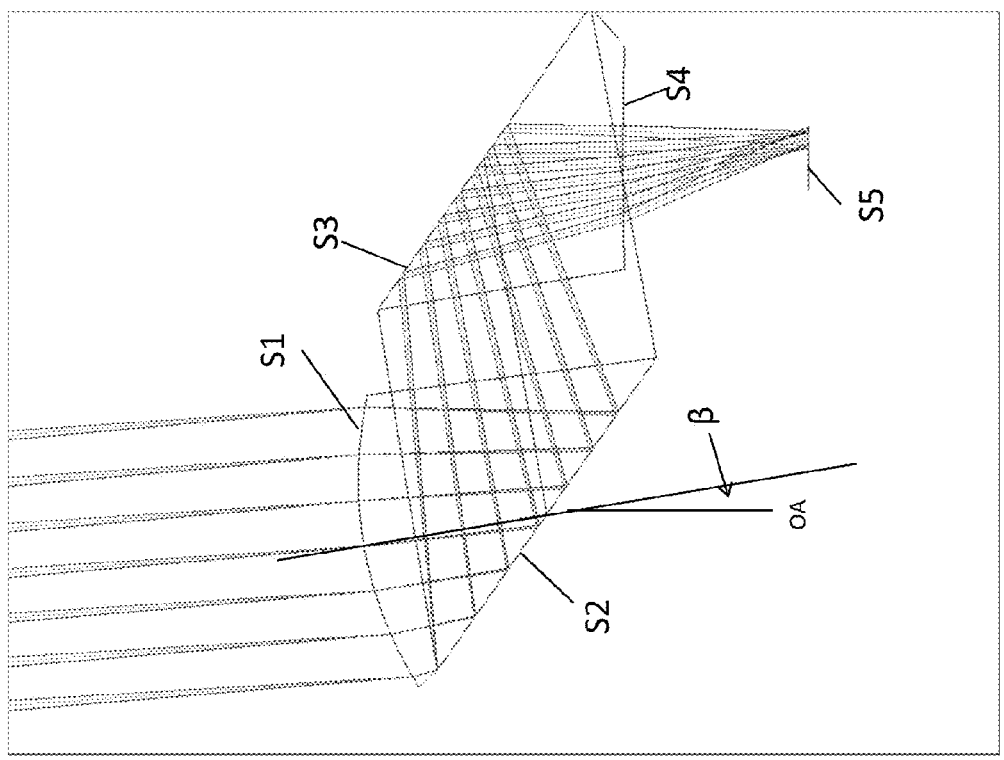
FIG. 6 is a cross section of one half of a binocular variant of the optical system to illustrate the tilting of the system relative to its optical axis.

In alternative embodiments, a binocular lens arrangement is provided. FIG. 5 shows a binocular version of the embodiment of FIG. 1; and FIG. 6 shows one half of a second binocular arrangement to illustrate the principle underlying the approach. In a binocular arrangement, the lens, reflecting member and sensors can be mounted rigidly within the acquisition device or a lens module within the acquisition device. However, the optical axis of at least the object side surface 13a, 13b; 13a' of the respective lens portions are rotated through an angle β away from the respective optical axes OA of the lens portions so that each lens portion can be directed towards and focused on a single eye of a face disposed in front of the optical system. In any case, this tilt allows each lens portion to have a greater depth of focus around the desired focus region—a given eye of a pair located, for example, at around 400 mm while retaining a minimal TTL.

In the example of FIG. 5, the optical system 10 of FIG. 1, is replicated to provide a first optical sub-system 50a and a second sub-system 50b, axially symmetric about a central axis CA. In the example of FIG. 5, each object side surface 13a, 13b has an aperture stop (AS) of approximately 3 mm. The distances indicated in the figure are: A=2 mm, B=3.9 mm, C=1.5 mm and D=2 mm. This provides a fixed focus lens F/2.15 and f=6.44 mm.

Each object side surface 13a, 13b and reflective surface 14a, 16a; 14b,16b are tilted at an angle β=1 degree with respect to their nominal optical axes OA (extending parallel to the central axis (CA)) and towards a respective eye within a face disposed in front of the optical system so allowing the eye to move a greater distance towards and away from the optical system around the nominal focus region than if the object side surfaces 13a, 13b were orthogonal to the optical axes OA. The image side surfaces 18a, 18b can remain symmetric about their respective parallel axes (PA).

It will be noted from the illustration of FIG. 5, that the image separation on the sensors 20a, 20b can be as little as approximately 2 mm and so it is possible to provide either a single image sensor receiving images from each sub-system 50a, 50b; or at least sensors formed on a common substrate.

Referring now to FIG. 6, again a fixed focus lens F/2.15 with f=6.44 mm and aperture stop diameter=3 mm is provided. In the example of FIG. 6, the angle of tilt for each of the surfaces S1, S2 and S3, in this case towards the left eye, is increased to β=10 degrees for illustration purposes.

FIG. 7 illustrates the aspheric coefficient values for each of the surfaces, especially S1-S5 of the system of FIG. 6. A different set of coefficients adjusted as appropriate can be used for the corresponding surfaces 13, 14, 16, 18 and 20 of the sub-systems 50a, 50b of FIG. 5.

For any of the above described embodiments, instead of moving either the lens or sensor to accommodate a user not facing the camera at a distance from the lens where their eye regions will be in focus, a software application can be provided which requests the user to move the device (in response to on-screen feedback) to the correct focal distance. (In such embodiments, the camera is disposed on the same surface of the acquisition device as a display screen.) Thus, either contrast or high frequency DCT coefficient information can be captured from an image stream to enable the application to determine when a user's face is at an optimal distance from the device and before an image on which iris recognition is to be based is captured.

The embodiments described above provide a dedicated optical system which can be incorporated within a thin image acquisition device to obtain IR images including a user's eye regions which can be used for user recognition and/or authentication.

The minimum depth of the optical system is a function of the aperture stop (AS) diameter which in the examples is approximately 3 mm—as the received image needs to be reflected transversely towards either a second reflective surface or reflective member 16, 16' and/or ultimately the image sensor 20 without obstruction. Where the image side surface 13 is positive, the first reflective surfaces 14 need extend by no more than the AS diameter from the image side surface 13. The optical distance from the second reflective surface or reflective member 16, 16' to the sensor plane 20 is typically half the TTL for non-folded optical systems and given that this in any case overlaps with the depth occupied by the first reflective surface 14, it will be seen that optical systems employing the above disclosed techniques can be provided within the minimal depth afforded by the relatively shallow housings of modern image acquisition devices including smartphones, tablets and laptop computers.

Figure 8:
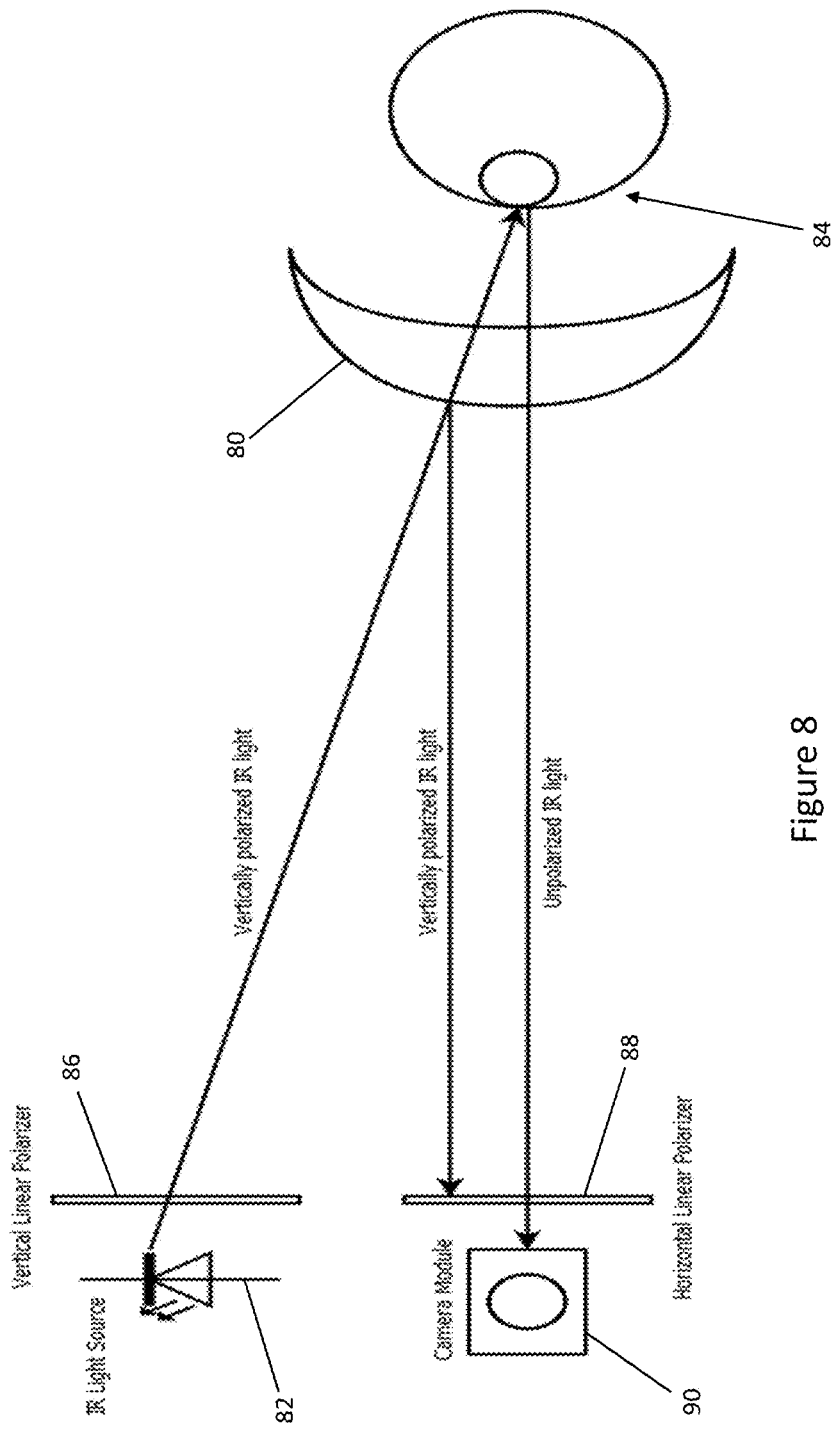
FIG. 8 illustrates an embodiment of the present invention including polarizers to mitigate problems with glare from glasses occluding an image of an iris.

In the above-described embodiments, each of the reflective surfaces 14 and 16 are flat. However, it will be appreciated that in variants of the embodiments and especially where the surfaces 14, 16 are provided on a molded surface of a lens, one or both of the reflective surfaces 14, 16 could be a curved spherical surface or a curved or flat surface with an asphericity according aspheric coefficients to improve the optical performance of the device. Referring now to FIG. 8, it will be appreciated that a common application for the optical systems described above is for acquiring IR images for use in iris based identification, typically to authenticate a user of a device. However, in many cases such users can be wearing glasses 80 which strongly reflect IR light. Thus, where an IR light source 82 is employed to illuminate a subject, the resultant glare from their glasses can completely occlude the subject's iris 84.

In some embodiments of the present invention, a set of linear polarizers 86, 88 are mounted in front of each of the IR light source 82 and an acquisition device camera module 90 including an optical system such as those described in relation to FIGS. 1-7 above. The angle between the polarization axis of the polarizer 86 mounted onto the IR light source 82 and the polarizer 88 mounted onto the camera module 90 is 90 degrees. Thus in one implementation based on an acquisition device in a conventional orientation, the first polarizer 86 would vertically polarize light, while the second polarizer 88 would horizontally polarize light.

This way, as long as light from the IR source 82 reflected by the glasses 80 does not change its polarization axis, the light reflected by the glasses, which is vertically polarized is filtered out by the horizontal linear polarizer 88 mounted onto the camera module 90. However, the light reflected by the eye, including the iris pattern 84, and skin which is un-polarized passes the horizontal linear polarizer 88 mounted onto the camera module 90 and so the iris pattern 84 can be imaged by the optical system.

An alternative to linear polarizers would be to use circular polarizers. In this case a polarizer mounted in front of the IR source 82 would have one sense, while a polarizer mounted in front of the camera module 90 would have an opposite sense. With the help of circular polarizers, IR reflections from surfaces could be removed, and they could also help improve the quality of the images acquired in natural light. So, if instead of the IR light source 82, a natural light source were being used, any polarizer mounted in front of the camera module 90 could be rotated electromechanically in order to achieve good quality images. It is nonetheless appreciated that providing such a rotation mechanism would increase the manufacturing costs for such a camera module.

For some biometric recognition applications, as well as acquiring an image including an iris pattern of sufficient resolution to enable identification, it can also be useful to acquire an image of a more complete face, so enabling user recognition based on an iris pattern to be supplemented with, or to follow, recognition based on other facial features (or vice versa).

While not limited to being implemented with the optical systems described above in relation to FIGS. 1-8, it will be appreciated that for an image acquisition device with an optical system with an angle of view just wide enough to capture an image including a sufficiently detailed iris pattern at a distance of say between 20-30 cm, a user may have to move the acquisition device to a distance in excess of 50 cm to obtain an image with a field of view wide enough to acquire a sufficiently complete image of a face for facial recognition. (Similar scaling applies to images for iris recognition captured at 40 cm.) Requiring a user to hold a device at distances in excess of 50 cm is not satisfactory and neither would requiring the user to move the device more than 20 cm between a position at less than 30 cm from their face to more than 50 cm from their face be acceptable for the purposes of performing biometric recognition.

Figure 9:
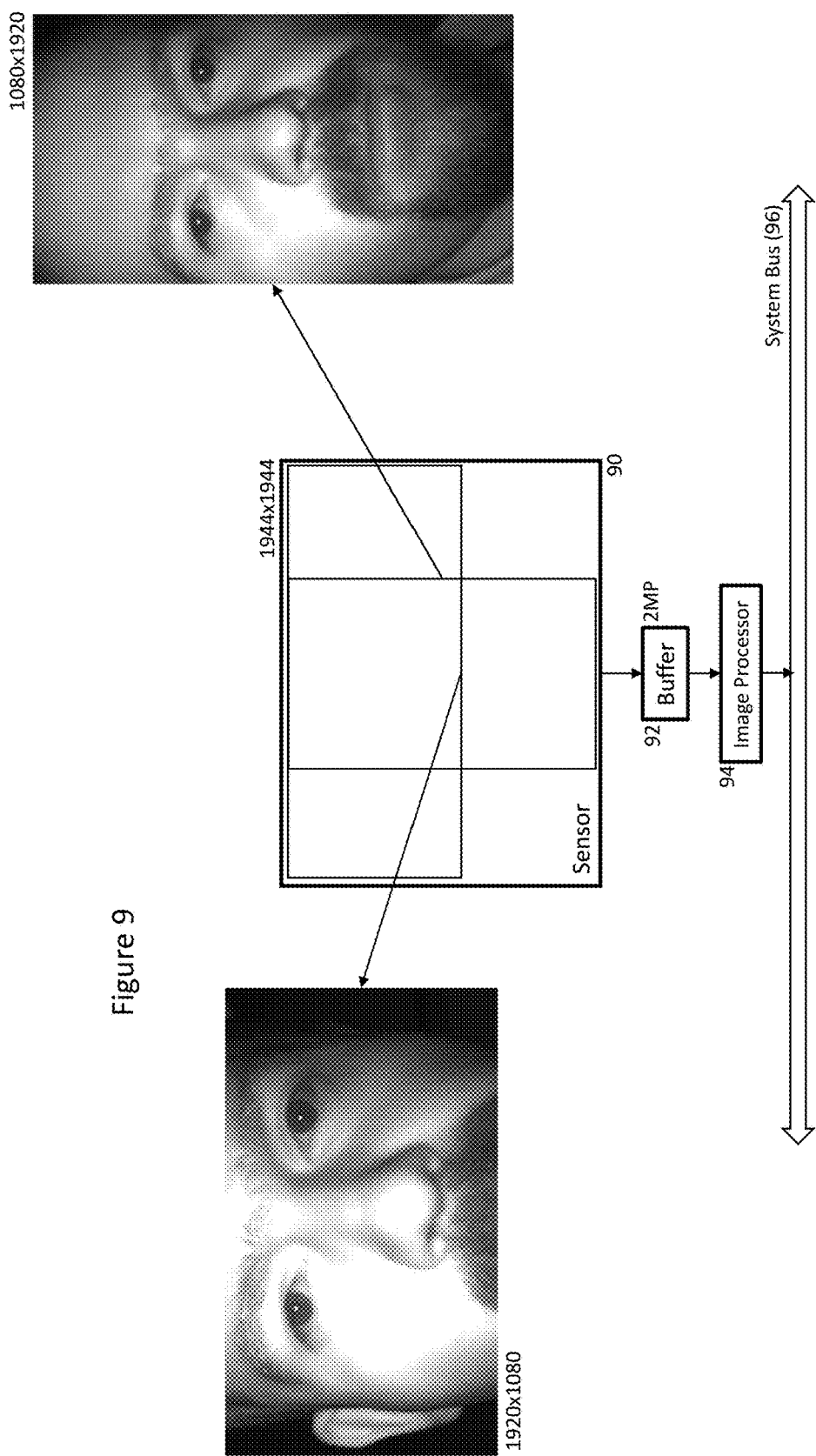
FIG. 9 illustrates an image processing system according to a further embodiment of the present invention.

Referring now to FIG. 9 there is shown an image processing system for an image acquisition device including an image sensor 90. In the embodiment, the sensor 90 comprises an Omnivision OV2281 sensor which can stream 2 MegaPixel images in either landscape or portrait mode. It will be appreciated nonetheless that the invention is not limited to being implemented with such a sensor and could equally be implemented with any equivalent sensor; and again the invention is not limited to being performed with the optical systems described in relation to FIGS. 1-8. The sensor 90 comprises 1944×1944 pixels (4 MP) but when in landscape mode, only 1920×1080 pixel values are read from the sensor into a 2 MP buffer 92; and, in portrait mode, only 1080×1920 pixel values covering a different area of the sensor are read into the buffer 92. In either case, the scene can be illuminated with an IR light source such as shown in FIG. 8 and the resultant image acquired can be an intensity image limited to IR wavelengths. These images are processed by an image processor 94 and can be written out onto a system bus 96 where they can be employed by other modules connected to the system bus 96; written into system memory (not shown); and/or used by applications running within the image processing system. Alternatively, the image processor 94 could include a biometric authentication unit (BAU) and could perform recognition internally before communicating its results via the bus 96. Using the exemplary sensor 90, the processor can be switched between providing landscape and portrait images in approximately 60 ms. Note that when switching between landscape and portrait mode, drivers within the system do not need to be re-loaded, the buffer size can stay the same, and the amount of transferred data is the same in both cases.

Using a sensor such as the sensor 90, it is possible to employ a given set of optics and to obtain images of sufficient resolution in landscape mode at distances of about 30 cm from a user to enable iris recognition; and to obtain images with sufficient field of view in portrait mode at distances of about 40 cm to enable facial recognition. In each case, processing can be performed on a smaller sized image than would be required to cover the entire field of view captured on the sensor 90 covering both the landscape and portrait images. So in the present example, a sensor comprising 4 MP requires processing circuitry capable of processing only 2 MP images to perform both iris and face based recognition of a subject. Biometric recognition based on swapping the sensor between landscape and portrait mode demands relatively little movement of the user between a location for obtaining an iris image and a location for obtaining a face recognition image and also the maximum distance required for obtaining a face recognition image, at approximately 40 cm, need not be unduly burdensome for the user. Note from the exemplary images illustrated in FIG. 9 that the field of view for the portrait image is actually wider than that of the landscape image because it has been captured with the user at a greater distance from the acquisition device.

Typically, a biometric recognition application running on the system shown might first capture one or more images for face recognition purposes at a distance of around 40 cm, a natural handheld position, with the sensor 90 configured in portrait mode. If a user's face is successfully recognized from the one or more images, the biometric recognition application can request the user to move the device closer to the face until the camera-subject distance is about 30 cm. While the user is moving the device closer, the sensor 90 is re-configured from portrait mode to landscape mode. Thus, at the required distance, one or more images suitable for iris recognition purposes can be captured and processed to attempt to recognize the user based on their iris pattern.

For any of the above described embodiments, fixed focus optics can be used, so that rather than adjusting focus to accommodate a user not facing the device at a distance where their eye/face regions will be in focus, the biometric recognition application can request the user to move the device to the correct distance. Typically, embodiments of the invention are implemented with a camera disposed on the same surface of the acquisition device as a display screen and while a request to have the user move the acquisition device between a position for acquiring a landscape iris recognition image and a portrait face recognition image can be performed in any way, this enables such requests to be provided through on-screen feedback. Either contrast or high frequency DCT coefficient information can be captured from an image stream to enable the biometric recognition application to determine when a user's eyes/face is at an optimal distance from the acquisition device and before an image on which iris or facial recognition is to be based is captured.

The invention claimed is:

1. An optical system for an image acquisition device comprising:

an image sensor comprising an array of pixels including pixels sensitive to IR wavelengths for acquiring an image; and multiple optical components formed in a single piece of plastic material, comprising a prism shape having first and second opposing surfaces and third and fourth opposing surfaces, formed along the prism shape to provide a lens assembly having a predetermined focal length, the lens assembly including:

a collecting lens having a convex surface positioned along the first surface to initially transmit light received from a scene along a first optical axis and then along a second axis transverse to the first optical axis for focusing on the image sensor, the lens assembly arranged to focus IR light received from a given object distance on a surface of the image sensor, the lens assembly further including:

a first reflective coating formed along the third surface for reflecting collected light along the second axis transverse to said first optical axis;

a second reflective coating formed along the fourth surface for further reflecting the collected light along a third axis parallel to the first optical axis; and a second lens positioned along the second surface to focus the collected light on the image sensor so that said optical system has a length, as measured along the first optical axis and the third axis, less than the predetermined focal length of the lens assembly.

2. The optical system according to claim 1 where the second reflective coating is positioned parallel spaced apart relationship to the first reflective coating and arranged to reflect light reflected from the first reflective coating toward the image sensor.

3. An optical system according to claim 2 wherein the second reflective coating is arranged to reflect light reflected from the first reflective coating through an image side surface, the image sensor being disposed in parallel spaced apart relationship to the fourth surface.

4. An optical system according to claim 2 wherein the collecting lens and the first surface are integrally formed in a first prism.

5. An optical system according to claim 4 wherein the third surface and the fourth surface are integrally formed in the first prism.

6. The optical system according to claim 4 wherein the third surface and the fourth surface are integrally formed in a second prism connected to the first prism, there being a gap formed between a portion of the first and second prisms.

7. An optical system according to claim 6 wherein said first and second prisms are integrally formed in a single mold.

8. An optical system according to claim 1, wherein said discrete lens is moveable along said transverse axis to focus said optical system.

9. An optical system according to claim 1 wherein the image sensor is moveable along one of the first optical axis or the third axis to focus the optical system.

10. An optical system according to claim 1 wherein an aperture stop diameter for the collecting lens is approximately 3 mm and wherein the optical system extends a depth of less than 5.5 mm from a front surface of the collecting lens to the image sensor.

11. A camera module including the optical system of claim 1.

12. An image acquisition system including a camera module according to claim 11 and further including a software application which is operable to determine if an image acquired by said camera module is in focus and, responsive to said image not being in focus, to direct a user to move the acquisition device to a correct focal distance from their face.

13. An image acquisition device including the camera module of claim 11 and an infra-red light source.

14. An image acquisition device according to claim 13 including a first polarizer mounted in front of said infra-red light source and a second polarizer mounted in front of said camera module.

15. An image acquisition device according to claim 14, wherein said polarizers are linear, each having respective polarization axes at 90 degrees to one another.

16. An image acquisition device according to claim 14, wherein said polarizers are circular, each having opposite polarization senses.

17. An image acquisition device according to claim 16 further comprising a mechanism for adjustably rotating said second polarizer.

18. A biometric recognition system including an image acquisition device comprising an optical system according to claim 1 and wherein the image sensor comprises X columns of Y pixels, said biometric recognition system further comprising:

a buffer operatively connected to the image sensor for selectively acquiring images from the sensor in one of landscape mode, where said images comprise A columns of B pixels, and portrait mode, where said images comprise C columns of D pixels, where $X \geq A > B$, $Y \geq D > C$, $X > C$ and $Y > B$; and a biometric recognition application operatively connected to said buffer for acquiring one or more images in portrait mode at a first distance of the image acquisition device from a subject sufficient to obtain an image of the subject's face for facial recognition and at a second distance, less than said first distance, of the image acquisition device from the subject sufficient to obtain at least one image of at least one of said subject's irises for iris recognition.

19. A biometric recognition system including an image acquisition device comprising an optical system according to claim 1 wherein said image sensor comprises X columns of Y pixels, and a buffer operatively connected to the image sensor for selectively acquiring images from the sensor in one of a landscape mode, where said images comprise A columns of B pixels, and a portrait mode, where said images comprise C columns of D pixels, where $X \geq A > B$, $Y \geq D > C$, $X > C$ and $Y > B$ and a biometric recognition application operatively connected to said buffer for acquiring one or more images in portrait mode at a first distance of the image acquisition device from a subject sufficient to obtain an image of the subject's face for facial recognition and at a second distance, less than said first distance, of the image acquisition device from the subject sufficient to obtain at least one image of at least one of said subject's irises for iris recognition.

20. A biometric recognition system as claimed in claim 19 comprising an optical system arranged to focus images at distances of between 30 cm and 40 cm between said image acquisition device and said subject on said image sensor.

21. A biometric recognition system as claimed in claim 19 comprising a fixed focus optical system.

22. A biometric recognition system as claimed in claim 19 wherein said image sensor comprises a 4 MP sensor and images captured in said landscape and said portrait modes comprises 2 MP images.

23. A biometric recognition system as claimed in claim 19 further comprising an infra-red illumination source.

\* \* \* \* \*